(12) United States Patent
Koop et al.

(10) Patent No.: US 9,596,854 B2
(45) Date of Patent: Mar. 21, 2017

(54) FUNGICIDAL PENFLUFEN MIXTURES

(71) Applicant: LANXESS Deutschland GmbH, Cologne (DE)

(72) Inventors: Bernd Koop, Cologne (DE); Martin Kugler, Leichlingen (DE); Thomas Jaetsch, Cologne (DE); Johannes Kaulen, Odenthal (DE); Tanja Gerharz, Duesseldorf (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 15/177,845

(22) Filed: Jun. 9, 2016

(65) Prior Publication Data

US 2016/0295863 A1 Oct. 13, 2016

Related U.S. Application Data

(62) Division of application No. 13/880,985, filed as application No. PCT/EP2011/067165 on Sep. 30, 2011, now abandoned.

(30) Foreign Application Priority Data

Oct. 25, 2010 (EP) .................................... 10188713
Nov. 4, 2010 (EP) .................................... 10190017

(51) Int. Cl.
| | | |
|---|---|---|
| *A01N 43/56* | (2006.01) |
| *B27K 3/34* | (2006.01) |
| *B27K 3/40* | (2006.01) |
| *A01N 31/08* | (2006.01) |
| *A01N 33/04* | (2006.01) |
| *A01N 33/12* | (2006.01) |
| *A01N 43/80* | (2006.01) |
| *A01N 55/08* | (2006.01) |
| *A01N 59/14* | (2006.01) |
| *A01N 47/12* | (2006.01) |

(52) U.S. Cl.
CPC ............. *A01N 43/56* (2013.01); *A01N 31/08* (2013.01); *A01N 33/04* (2013.01); *A01N 33/12* (2013.01); *A01N 43/80* (2013.01); *A01N 47/12* (2013.01); *A01N 55/08* (2013.01); *A01N 59/14* (2013.01); *B27K 3/343* (2013.01); *B27K 3/40* (2013.01); *B27K 2240/20* (2013.01)

(58) Field of Classification Search
CPC ........ A01N 43/56; A01N 59/14; A01N 33/04; A01N 33/12; A01N 43/80; A01N 31/16; A01N 47/12; A01N 31/08; A01N 55/08; B27K 3/343; B27K 3/40
See application file for complete search history.

(56) References Cited

U.S. PATENT DOCUMENTS

| | | | | |
|---|---|---|---|---|
| 7,538,073 B2 * | 5/2009 | Elbe | ..................... | C07D 231/16 504/280 |
| 2005/0053516 A1 * | 3/2005 | Whitaker | ............. | A01N 1/0215 422/28 |
| 2011/0124501 A1 * | 5/2011 | Cristau | .................. | A01N 43/78 504/100 |

FOREIGN PATENT DOCUMENTS

DE    CA 2862939 A1 *    5/2005    ............. A01N 37/22

* cited by examiner

*Primary Examiner* — Timothy Thomas
*Assistant Examiner* — Andrew S Rosenthal

(57) ABSTRACT

Fungicidal mixtures having synergistic fungicidal activity may include penflufen and at least one further fungicidal material. The mixtures may be used for protecting industrial materials, and methods for treating industrial materials with the penflufen mixtures are provided.

9 Claims, No Drawings

FUNGICIDAL PENFLUFEN MIXTURES

CROSS REFERENCE TO RELATED PATENT APPLICATIONS

This application is a divisional of pending U.S. patent application Ser. No. 13/880,985 filed Dec. 11, 2013, entitled "FUNGICIDAL PENFLUFEN MIXTURES, which claims the right of priority under 35 U.S.C. §119 (a)-(d) and 35 U.S.C. §365 of International Application No. PCT/EP20111/067165, filed 30 Sep. 2011, which is entitled to the right of priority of European Patent Application No. DE 10188713.1, filed on 25 Oct. 2010, the contents of which are hereby incorporated by reference in their entirety.

The invention relates to mixtures comprising penflufen, to the use of these mixtures for protecting industrial materials and to a method for treating industrial materials with the penflufen mixtures.

Penflufen (N-(2-[1,3-dimethylbutylphenyl]-5-fluoro-1,3-dimethyl-1H-pyrazole-4-carboxamide) is a pyrazolylcarboxanilide of the formula (I). In addition, penflufen is a fungicide.

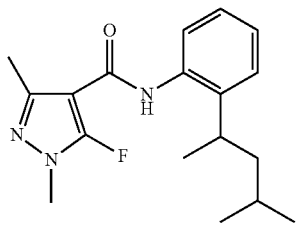

(I)

Pyrazolylcarboxanilides are specific carboxamides and are known from WO 03/010149 for controlling unwanted microorganisms in crop protection and in the protection of materials. WO 03/010149 mentions penflufen in a list of further pyrazolylcarboxanilides, and the action of penflufen as a crop protection agent is shown in one example. Specific mixtures with penflufen have not been described.

WO 2006/114212 discloses active compound combinations of carboxamides with known insecticidally active compounds for controlling unwanted animal pests and also unwanted phytopathogenic fungi. Mixtures of penflufen and insecticides have also been described.

Further active compound combinations of penflufen and insecticides are known from WO 2009/098225 A2.

Synergistic fungicidal active compound combinations comprising carboxamides with a wide variety of different mixing partners are known from WO 2005/041653. Here, too, penflufen is, among others, mentioned as a mixing partner. The use described of the synergistic fungicidal active compound combinations is the control of phytopathogenic fungi.

Furthermore, from WO2009/098218 and WO2009/090181 it is known to use carboxamides for crop protection and for the protection of materials.

WO 2005/058839 discloses a wide variety of different fungicides, bactericides and insecticides which may be used, optionally with an optically active carboxamide, for example an enantiomer of penflufen, for controlling unwanted microorganisms in crop protection and in the protection of industrial materials. Specific examples of mixtures are not mentioned. One example shows the use of an optically active enantiomer of penflufen for crop protection.

Further active compound combinations which may, among others, comprise penflufen are known from WO 2007/110173 and WO 2008/014955.

The known active compound combinations have the disadvantage that their activity against microorganisms is not always sufficient in the protection of materials.

Accordingly, there is a need for further active compound combinations which offer industrial materials, in particular wood, timber or wood/plastics composites, particular protection against microorganisms.

Surprisingly, we have found novel synergistic active compound combinations which comprise penflufen and overcome the disadvantages of the prior art.

Accordingly, the invention provides compositions comprising
a) penflufen and its salts or acid addition compounds and
b) at least one compound selected from the group consisting of phenols, boron compounds, compounds of the formula (II)

$$((R^1R^2R^3R^4)N)_nX \quad (II)$$

where
$R^1$ and $R^2$ may be identical or different and independently of one another represent $C_3$-$C_6$-alkyl and
$R^3$ and $R^4$ may be identical or different and independently of one another are selected from the group consisting of $C_6$-$C_{22}$-alkyl, $C_6$-$C_{22}$-alkenyl, $C_6$-$C_{24}$-aryl, $C_3$-$C_{20}$-cycloalkyl and radicals of the formula (IV)

$$-[CH_2-CH_2-O]_z-CH_2-CH_2-OH \quad (IV)$$

where z=1, 2, 3, 4, 5, 6, 7, 8, 9 or 10 and
X represents an anion carrying a charge of n and
n is an integer greater than zero,
isothiazolinones, 3-iodo-2-propynyl alkylcarbamates, 3-iodo-2-propynyl cycloalkylcarbamates, 3-iodo-2-propynyl arylcarbamate and compounds of the formula (II)

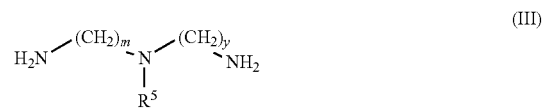

(III)

in which
$R^5$ represents $C_8$-$C_{18}$-alkyl, $C_8$-$C_{18}$-alkenyl or $C_5$-$C_{20}$-cycloalkyl and
m and y may be identical or different and represent a number 1, 2, 3, 4, 5 or 6, and their acid addition compounds.

Penflufen may be employed as a racemate, in enantiomerically pure form or as an enriched enantiomer mixture. A use as salt or acid addition compound is also possible, salts being understood as meaning in particular sodium, potassium, magnesium, calcium, zinc, aluminium, iron and copper salts, and acid addition compounds being understood as meaning in particular adducts with hydrohalic acids, for example hydrogen chloride and hydrogen bromide, carboxylic acids such as, for example, formic acid, acetic acid, tartaric acid and oxalic acid, sulphonic acids such as, for example, p-toluenesulphonic acid, and also sulphuric acid, phosphoric acid and nitric acid.

The phenols are preferably tribromophenol, tetrachlorophenol, 3-methyl-4-chlorophenol, 3,5-dimethyl-4-chlorophenol, dichlorophen, 2-benzyl-4-chlorophenol, triclosan, diclosan, hexachlorophene, p-hydroxybenzoic esters, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and their alkali and alkaline earth metal salts, or mixtures of these compounds. Particularly preferably, the phenols used are phenylphenols. Very particular preference is given to using o-phenylphenol.

The boron compounds are preferably inorganic boron compounds. Particularly preferably, the boron compounds are alkali metal or alkaline earth metal borates such as, for example, sodium tetraborate, disodium tetraborate decahydrate (sodium borate, borax) or disodium octaborate tetrahydrate, or boric acid, boron oxide, boric hydrides, or boric esters or mixtures of these compounds. Very particular preference is given to using mixtures with boron oxide, borax and boric acid.

The compounds of the formula (II) are organic quarternary ammonium compounds. Preferably, the compounds of the formula (II) are benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, hexadecyltrimethylammonium chloride, didecylmethylpoly(oxyethyl)ammonium propionate, didecyldimethylammonium carbonate, didecyldimethylammonium bicarbonate. Particular preference is given to mixtures with didecylmethylpoly(oxyethyl) ammonium propionate, benzalkonium chloride, didecyldimethylammonium chloride, didecyldimethylammonium carbonate and didecyldimethylammonium bicarbonate.

The radicals of the formula (IV) are derivatives of polyethylene glycols.

z is preferably 2, 3, 4 or 5.

$R^1$ and $R^2$ independently of one another preferably represent methyl, ethyl, n-propyl, isopropyl, n-butyl, sec-butyl, tert-butyl or n-pentyl. Particularly preferably, $R^1$ or $R^2$ represent methyl.

$R^3$ and $R^4$ independently of one another preferably represent phenyl, benzyl, o-, m-, p-xylene, o-, m-, p-trimethylphenyl, o-, p-, m-chlorobenzyl, —$CH_2$—$CH_2$—O—$CH_2$—$CH_2OH$, —[$CH_2$—$CH_2$—O]$_2$—$CH_2$—$CH_2$—OH, —[$CH_2$—$CH_2$—O]$_3$—$CH_2$—$CH_2$—OH, —[$CH_2$—$CH_2$—O]$_4$—$CH_2$—$CH_2$—OH, dichlorobenzyl, n-isononyl, n-isodecyl, n-isododecyl, n-isotetradecyl, n-isohexadecyl, n-isooctenyl, n-isononenyl, or n-isodecenyl. Particularly preferably, $R^3$ and $R^4$ independently of one another represent benzyl, —$CH_2$—$CH_2$—O—$CH_2$—$CH_2$—OH, —[$CH_2$—$CH_2$—O]$_2$—$CH_2$—$CH_2$—OH, —[$CH_2$—$CH_2$—O]$_3$—$CH_2CH_2$—OH, —[$CH_2$—$CH_2$—O]$_4$—$CH_2CH_2$—OH, dichlorobenzyl, n-isononyl, n-isodecyl, n-isododecyl, n-isotetradecyl, n-isohexadecyl, n-isooctenyl, n-isononenyl, or n-isodecenyl.

X preferably represents a halide, carbonate, bicarbonate, borate, sulphate, hydroxide or carboxylate. Particularly preferably, X represents a chloride, bicarbonate or carbonate.

n is preferably 1, 2 or 3.

The isothiazolinones are preferably N-methylisothiazolin-3-one, 5-chloro-N-methylisothiazolin-3-one, 4,5-dichloro-N-octylisothiazolin-3-one (DCOIT), 5-chloro-N-octylisothiazolinone, N-octylisothiazolin-3-one, 4,5-trimethyleneisothiazolinone and 4,5-benzisothiazolinone. The isothiazolinone used is with particular preference 4,5-dichloro-N-octylisothiazolin-3-one (DCOIT).

3-Iodo-2-propynyl alkylcarbamate preferably represents 3-iodo-2-propynyl N-butylcarbamate (IPBC) and 3-iodo-2-propynyl N-hexylcarbamate. 3-Iodo-2-propynyl alkylcarbamate particularly preferably represents 3-iodo-2-propynyl N-butylcarbamate.

3-Iodo-2-propynyl cycloalkylcarbamate preferably represents 3-iodo-2-propynyl cyclohexylcarbamate.

3-Iodo-2-propynyl arylcarbamate preferably represents 3-iodo-2-propynyl N-phenylcarbamate.

The compounds of the formula (I) are tertiary amines. With particular preference, the compounds of the formula (III) are N-(3-aminopropyl)-N-dodecyl-1,3-propanediamine, N-(3-aminopropyl)-N-decyl-1,3-propanediamine, N-(3-aminopropyl)-N-tetradecyl-1,3-propanediamine and their acid addition compounds.

Acid addition compounds of the compounds of the formula (III) are to be understood as meaning, in particular, adducts with hydrohalic acids, for example hydrogen chloride and hydrogen bromide, carboxylic acids such as, for example, formic acid, acetic acid, tartaric acid and oxalic acid, sulphonic acids such as, for example, p-toluenesulphonic acid, and also sulphuric acid, phosphoric acid and nitric acid.

$R^5$ preferably represents n-isooctyl, n-isononyl, n-isodecyl, n-isododecyl, n-isohexadecyl, n-isooctenyl, n-isononenyl, n-isodecenyl, cyclopentyl or cyclohexyl.

With particular preference, $R^5$ represents dodecyl, tetradecyl or decyl.

m preferably represents 2, 3 or 4. y preferably represents 2, 3 or 4.

Alkyl and alkenyl in each case independently represent straight-chain, cyclic or branched alkyl and alkenyl radicals, respectively.

$C_1$-$C_6$-Alkyl represents, for example, methyl, ethyl, n-propyl, isopropyl, n-butyl, sec-butyl, tert-butyl, n-pentyl, i-methylbutyl, 2-methylbutyl, 3-methylbutyl, neopentyl, 1-ethylpropyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and 1-ethyl-2-methylpropyl. Preferably, $C_1$-$C_6$-alkyl represents methyl, ethyl, n-propyl, isopropyl, n-butyl, sec-butyl, tert-butyl, n-pentyl, 1-methylbutyl and n-hexyl. $C_8$-$C_{18}$-Alkyl and/or $C_6$-$C_{22}$-alkyl represent, by way of example and preferably, n-isooctyl, n-isononyl, n-isodecyl, n-isododecyl, or n-isohexadecyl.

By way of example and preferably. $C_8$-$C_{18}$-alkenyl and/or $C_6$-$C_{22}$-alkenyl represent n-isooctenyl, n-isononenyl, or n-isodecenyl or else also represent polyunsaturated $C_8$-$C_{18}$-alkenyl radicals.

By way of example and preferably, $C_5$-$C_{20}$-cycloalkyl represents cyclopentyl or cyclohexyl.

In the context of the invention, $C_6$-$C_{20}$-aryl represents a mono-, bi- or tricyclic carbocyclic aromatic radical which has preferably 6 to 24 aromatic carbon atoms and which may optionally be substituted further by halogens. By way of example and preferably, $C_6$-$C_{24}$-aryl represents biphenyl, phenyl, o-, p-, m-chlorobenzyl, dichlorobenzyl, naphthyl, o-, m-, p-benzyl, o-, m-, p-xylene or o-, m-, p-trimethylphenyl. Particularly preferably, $C_6$-$C_{24}$-aryl represents o-, m-, p-benzyl, o-, p-, m-chlorobenzyl or dichlorobenzyl.

Preference is given to compositions comprising
a) penflufen and its salts or acid addition compounds
   and
b) at least one compound selected from the group of
   the phenols:
   tribromophenol, tetrachlorophenol, 3-methyl-4-chlorophenol, 3,5-dimethyl-4-chlorophenol, dichlorophen, 2-benzyl-4-chlorophenol, triclosan, diclosan, hexachlorophene, p-hydroxybenzoic esters, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and their alkali metal and alkaline earth metal salts;
   the borates:
   alkali metal borates, alkaline earth metal borates, boric acid, boron oxide, boric anhydride, or boric esters,
   the organic, quaternary ammonium compounds: benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, hexadecyltrimethylammonium chloride, didecylmethylpoly(oxyethyl)ammonium propionate, didecyldimethylammonium carbonate, didecyldimethylammonium bicarbonate, 1-hexadecylpyridinium chloride
   the isothiazolinones:
   N-methylisothiazolin-3-one, 5-chloro-N-methylisothiazolin-3-one, 4,5-dichloro-N-octylisothiazolin-3-one (DCOIT), 5-chloro-N-octylisothiazolinone, N-octylisothiazolin-3-one, 4,5-trimethylene-isothiazolinone and 4,5-benzisothiazolinone,
   the carbamates:
   3-iodo-2-propynyl N-butylcarbamate, 3-iodo-2-propynyl N-hexylcarbamate, 3-iodo-2-propynyl cyclohexylcarbamate,
   the tertiary amines:
   N-(3-aminopropyl)-N-dodecylpropane-1,3-diamine,
   N-(3-aminopropyl)-N-decylpropane-1,3-diamine,
   N-(3-aminopropyl)-N-tetradecylpropane-1,3-diamine.
Particular preference is given to compositions comprising
a) penflufen and its salts or acid addition compounds
   and
b) at least one compound selected from the group consisting of o-phenylphenol, m-phenylphenol, p-phenylphenol and their alkali metal and alkaline earth metal salts
   sodium borate, boric acid, boron oxide, boric anhydride, boric esters,
   benzalkonium chloride, didecyldimethylammonium chloride, didecylmethylpoly(oxyethyl)ammonium propionate, didecyldimethylammonium carbonate, didecyldimethylammonium bicarbonate,
   4,5-dichloro-N-octylisothiazolin-3-one,
   3-iodo-2-propynyl N-butylcarbamate,
   N-(3-aminopropyl)-N-dodecylpropane-1,3-diamine.
Very particular preference is given to compositions comprising
a) penflufen and its salts or acid addition compounds
   and
b) at least one compound selected from the group consisting of o-phenylphenol and its alkali metal and alkaline earth metal salts
   sodium borate, boric acid, boron oxide, mixtures with boron oxide, borax and boric acid
   benzalkonium chloride, didecyldimethylammonium chloride, didecylmethylpoly(oxyethyl)ammonium propionate, didecyldimethylammonium carbonate, didecyldimethylammonium bicarbonate or a mixture of didecyldimethylammnonium carbonate and didecyldimethylammonium bicarbonate (Carboquat)
   4,5-dichloro-N-octylisothiazolin-3-one,
   3-iodo-2-propynyl N-butylcarbamate,
   N-(3-aminopropyl)-N-dodecylpropane-1,3-diamine.
The following compositions are even more preferred:

TABLE 1

| Mixing partner a) penflufen | Mixing partner b) |
| --- | --- |
| penflufen | sodium borate |
| penflufen | boric acid |
| penflufen | boron oxide |
| penflufen | benzalkonium chloride |
| penflufen | didecyldimethylammonium chloride |
| penflufen | didecyldimethylammonium carbonate and didecyldimethylammonium bicarbonate (Carboquat) |
| penflufen | didecylmethylpoly(oxyethyl)ammonium propionate |
| penflufen | 4,5-dichloro-N-octylisothiazolin-3-one |
| penflufen | 3-iodo-2-propynyl N-butylcarbamate |
| penflufen | N-(3-aminopropyl)-N-dodecyl-1,3-propanediamine |
| penflufen | o-phenylphenol |

The scope of the invention includes all general radical definitions, parameters and illustrations mentioned above and below, and those mentioned in preferred ranges, with one another, i.e. also any combinations between the respective ranges and preferred ranges.

A particularly high synergistic activity of the mixtures mentioned above was found in particular directly on the impregnated wood or timber products, and also on the wood/plastic composites.

Penflufen is preferably employed in a weight ratio of 50:1 to 1:50, in particular of from 20:1 to 1:20, preferably of from 10:1 to 1:10 to a compound of b) (Table 1).

In addition, a particular synergistic activity of penflufen with 3-iodo-2-propynyl N-butylcarbamate and with 4,5-dichloro-N-octylisothiazolin-3-one was found at certain weight ratios.

Accordingly, particular preference is given to a composition of penflufen and 3-iodo-2-propynyl-N-butylcarbamate which comprises 85% by weight to 75% by weight of penflufen and 15% by weight to 25% by weight of 3-iodo-2-propynyl-N-butylcarbamate.

Particularly preferably, the compositions of penflufen and isothiazolinones comprise more than 50% by weight of penflufen. Very particularly preferably, the mixtures comprise at least 50% by weight of penflufen and at least 10% by weight of 4,5-dichloro-N-octylisothiazolin-3-one.

The compositions used in accordance with the invention can be employed in solid or liquid form. Suitable for this purpose are formulations such as solutions, emulsions, suspensions, powders, granules, pastes, aerosols and also very fine encapsulations in polymeric substances.

Such formulations can be produced in a known manner, for example by mixing the compositions with extenders, that is liquid solvents, liquefied gases under pressure, and/or solid carriers, optionally with the use of surfactants, that is emulsifiers and/or dispersants, and/or foam formers. If the extender used is water, it is also possible to employ organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycerol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as knolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks. Suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and protein hydrolysates. Suitable dispersants are: for example lignosulphite waste liquors and methylcellulose.

Tackifiers, such as carboxymethyl cellulose, natural and synthetic polymers in the form of powders, granules or latices, such as gum arabic, polyvinyl alcohol and polyvinyl acetate, and also natural phospholipids, such as cephalins and lecithins, and synthetic phospholipids can additionally be used in the formulations. Further additives may be mineral and vegetable oils.

The compositions may furthermore comprise colorants such as inorganic pigments, for example iron oxide, titanium oxide, Prussian Blue, copper oxide and organic dyes, such as alizarin, azo and metallophthalocyanine dyes.

The composition used generally comprises preferably from 0.1 to 95 percent by weight of components a) and b), preferably from 0.5 to 90% by weight.

The compositions according to the invention may also comprise other active compounds, for example fungicides, bactericides and/or insecticides, to broaden the activity spectrum or to prevent the development of resistance, for example. In many cases, synergistic effects are obtained, i.e. the activity of combined active compounds is greater than the activity of the individual components.

Particularly favourable co-components in mixtures are, for example, the following compounds:

triazoles such as:
azaconazole, bitertanol, bromuconazole, cyproconazole, diclobutrazol, difenoconazole, diniconazole, epoxyconazole, etaconazole, fenbuconazole, fluquinconazole, flusilazole, flutriafol, furconazole, hexaconazole, imibenconazole, ipconazole, myclobutanil, metconazole, penconazole, propiconazole, prothioconazole, simeconazole, tebuconazole, tetraconazole, triadimefon, triadimenol, triticonazole and uniconazole and their metal salts and acid adducts;

imidazoles such as:
clotrimazole, bifonazole, climbazole, econazole, fenapanil, imazalil, isoconazole, ketoconazole, lombazole, miconazole, pefurazoate, prochloraz, triflumizole and their metal salts and acid adducts;

pyridines and pyrimidines such as:
ancymidol, buthiobate, fenarimol, mepanipyrin, nuarimol, pyroxyfur, triamirol; succinate dehydrogenase inhibitors such as:

benodanil, bixafen, boscalid, carboxim, carboxim sulphoxide, cyclafluramid, fenfuram, flutanil, furametpyr, furcarbanil, furmecyclox, mebenil, mepronil, methfuroxam, metsulphovax, nicobifen, pyrocarbolid, oxycarboxin, Shirlan, Secedvax;

naphthalene derivatives such as:
terbinafine, naftifine, butenafine, 3-chloro-7-(2-aza-2,7,7-trimethyl-oct-3-en-5-ine);

sulphenamides such as:
dichlofluanid, tolylfluanid, folpet, fluorofolpet, captan, captofol;

benzimidazoles such as:
carbendazim, benomyl, fuberidazole, thiabendazole or their salts;

morpholine derivatives such as:
aldimtorph, dimethomorph, dodemorph, falimorph, fenpropidin fenpropimorp, tridemorph, trimorphamid and their arylsulphonate salts such as, for example, p-toluenesulphonic acid and p-dodecylphenyl-sulphonic acid;

benzothiazoles such as:
2-mercaptobenzothiazole;

benzothiophene dioxides such as:
N-cyclohexylbenzo[b]thiophenecaiboxamide S,S-dioxide;

benzamides such as:
2,6-dichloro-N-(4-trifluoromethylbenzyl)benzamide, tecloftalam;

boron compounds such as:
boric acid, boric ester, borax;

formaldehyde and formaldehyde-releasing compounds such as:
benzyl alcohol mono-(poly)-hemiformal, n-butanol hemiformal, dazomet, ethylene glycol hemiformal, hexa-hydro-S-triazine, hexamethylenetetramine, N-hydroxymethyl-N'-methylthiourea. N-methylolchloroacetamide, oxazolidine, paraformaldehyde, taurolin, tetrahydro-1,3-oxazine, N-(2-hydroxypropyl)-amine-methanol, tetramethylol acetylenediurea;

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone. N-octylisothiazolin-3-one, 4,5-trimethyleneisothiazolinone, 4,5-benzisothiazolinone;

aldehydes such as:
cinnamnaldehyde, formaldehyde, glutardialdehyde, β-bromocinnamaldehyde, o-phthaldialdehyde;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzylimethyldodecylammonium chloride, dichlorobenzyldimethylalkylammonium chloride, didecyldimethylammonium chloride, dioctyldimethylammonium chloride, N-hexadecyltrimethylammonium chloride, 1-hexadecylpyridinium chloride, iminoctadine tris(albesilate);

iodine derivatives such as:
diiodomethyl p-tolyl sulphone, 3-iodo-2-propynyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propynyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;

phenols such as:

tribromophenol, tetrachlorophenol, 3-methyl-4-chlorophenol, 3,5-dimethyl-4-chlorophenol, dichlorophen, 2-benzyl-4-chlorophenol, triclosan, diclosan, hexachlorophene, p-hydroxybenzoic esters, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and their alkali and alkaline earth metal salts;

microbicides with an activated halogen group such as:

bronopol, bronidox, 2-bromo-2-nitro-1,3-propanediol, 2-bromo-4'-hydroxyacctophenone, 1-bromo-3-chloro-4,4,5,5-tetramethyl-2-imidazolidinone, β-bromo-β-nitrostyrene, chloroacetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrile-propionamide, 1,2-dibromo-2,4-dicyanobutane, halane, halazone, mucochloric acid, phenyl (2-chlorocyanovinyl) sulphone, phenyl (1,2-dichloro-2-cyanovinyl) sulphone, trichloroisocyanuric acid;

pyridines such as:

1-hydroxy-2-pyridinethione (and their Cu, Na, Fe, Mn, Zn salts), tetrachloro-4-methylsulphonylpyridine, pyrimethanol, mepanipyrim, dipyrithione, 1-hydroxy-4-methyl-6-(2,4,4-trimethylpentyl)-2(1H)-pyridine;

methoxyacrylates or similar such as:

azoxystrobin, dimoxystrobin, fluoxastrobin, kresoximmethyl, metominostrobin, orysastrobin, picoxystrobin, pyraclostrobin, trifloxystrobin;

metal soaps such as:

salts of the metals tin, copper and zinc with higher fatty acids, resin acids, naphthenoic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:

salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate; oxides such as:

oxides of the metals tin, copper and zinc, such as, for example, tributyltin oxide, $Cu_2O$, CuO, ZnO;

oxidizing agents such as:

hydrogen peroxide, peracetic acid, potassium persulphate;

dithiocarbamates such as:

cufraneb, ferban, potassium N-hydroxymethyl-N'-methyldithiocarbamate, sodium dimethyldithiocarbamate, potassium dimethyldithiocarbamate, mancozeb, maneb, metam, metiram, thiram, zineb, ziram;

nitriles such as:

2,4,5,6-tetrachloroisophthalonitrile, disodium cyanodithioimidocarbamate;

quinolines such as:

8-hydroxyquinoline and its copper salts:

other fungicides and bactericides such as:

bethozaxin, 5-hydroxy-2(5H)-furanone, 4,5-benzodithiazolinone, 4,5-trimethylenedithiazolinone, N-(2-p-chlorobenzoylethyl)hexaminium chloride, 2-oxo-2-(4-hydroxyphenyl)acetohydroxycinnamoyl chloride, tris-N-(cyclohexyldiazeniumdioxy)aluminium, N-(cyclohexyldiazeniumdioxy)tributyltin or its potassium salts, bis-N-(cyclohexyldiazeniumdioxy)copper, iprovalicarb, fenhexamide, spiroxamine, carpropamid, diflumetorin, quinoxyfen, famoxadone, polyoxorim, acibenzolar S-methyl, furametpyr, thifluzamide, methalaxyl-M, benthiavalicarb, metrafenone, cyflufenamid, tiadinil, tea tree oil, phenoxyethanol.

Ag-, Zn- or Cu-containing zeolites alone or incorporated into polymeric materials.

Insecticides:

abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtin, azinphos A, azinphos M, azocyclotin,

*Bacillus thuringiensis*, barthrin, 4-bromo-2-(4-chlorophenyl)-1-(ethoxymethyl)-5-(tnifluozromethyl)-1H-pyrrole-3-carbonitrile, bendiocarb, benfuracarb, bensultap, betacyfluthrin, bifenthrin, bioresmethrin, bioallcthrin, bistrifluron, bromophos A, bromnophos M, bufencarb, buprofezin, butathiophos, butocarboxim, butoxycarboxim, cadusafos, carbaryl, carbofuran, carbophenothion, carbosulphan, cartap, chinomethionat, cloethocarb, 4-chloro-2-(2-chloro-2-methylpropyl)-5-[(6-iodo-3-pyridinyl)methoxy]-3(2H)-pyridazinone (CAS-RN: 120955-77-3), chlordane, chlorethoxyfos, chlorfenapyr, chlorfenvinphos, chlorfluazuron, chlormephos, N-[(6-chloro-3-pyridinyl)methyl]-N'-cyano-N-methylethaneimidamide, chlorpicrin, chlorpyrifos A, chlorpyrifos M, cis-resmethrin, clocythrin, clothiazoben, cypophenothrin, clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1-(1,1-dimehtyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl(4-ethoxyphenyl)silylmethyl-3-phenoxybenzyl ether, dimethylvinphos, dioxathion, disulphoton, eflusilanate, emamectin, empenthrin, endosulphan, O-ethyl O-(4-nitrophenyl) P-phenylphosphonothioate, esfenvalerate, ethiofencarb, ethion, etofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximate, fensulphothion, fenthion, fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan, fosthiazate, fubfenprox, furathiocarb halofenocid, HCH (CAS RN: 58-89-9), heptenophos, hexaflumuron, hexythiazox, hydramethylnon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, lamacyhalothrin, lufenuron, kadedrin, lambda-cyhalothrin, lufenuron, malathion, mecarbam, mervinphos, mesulphenphos, metaldehyde, methacrifos, methamidophos, methidathion, methiocarb, methomyl, metalcarb, milbemectin, monocrotophos, moxiectin, naled, nicotine, nitenpyram, noviflumuron, omethoate, oxamyl, oxydemethon M, oxydeprofos, parathion A, parathion M, penfluron, permethrin, 2-(4-phenoxyphenoxy)-ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethnum, pyridaben, pyridalyl, pyrimidifen, pyriproxifen, pyrithiobac-sodium, quinalphos, resmethrin, rotenone, salithion, sebufos, silafluofen, spinosad, spirodiclofen, spiromesifen, sulphotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron, trichlorfon, triflumuron, trimethacarb, vamidothion, xylylcarb, zetamethrin;

herbicides and other algicides:

acetochlor, acifluorfen, aclonifen, acrolein, alachlor, alloxydim, ametryn, amidosulphuron, amitrole, ammonium sulphamate, anilofos, asulam, atrazine, azafenidin, aziptrotryne, azimsulphuron, benazolin, benfluralin, benfuresate, bensulphuron, bensulphide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulphuron, chlorthal, chlorthiamid, cinmethylin, cinofulsuron, clefoxydim, clethodim, clomazone, chlomeprop, clopyralid, cyanamide, cyanazine, cybutryne, cycloate, cycloxydim, chloroxynil, clodinaifop-propargyl, cumyluron, clometoxyfen, cyhalofop, cyhalofop-butyl, clopyrasuluron, cyclosulphamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diuron, DNOC (2-methyl-4, 6-dinitrophenol), DSMA (disodium methylarsonate), (2,4-dichlorophenoxy)acetic acid, daimuron, dalapon, dazomnet, 2,4-DB (4-(2,4-dichlorophenoxy)butanoic acid), desmedipham, desmetryn, dicamba, dichlobenil, dimethamid, dithiopyr, dimethametryn, eglinazine, endothal, EPIC (S-ethyl dipropylthiocarbamate), esprocarb, ethalfluralin, ethidimuron, ethofumesate, ethobenzanid, etlioxyfen, ethametsulphuron, ethoxysuiphuron, fenoxaprop, fenoxaprop-P, fenuron, flamprop, flamprop-M, flazasuiphuron, fluazifop, fluazifop-P, fuenachlor, fluchloralin, flufenacet, flumeturon, fluorocglycofen, fluoronitrofen, flupropanate, flurenol, fluridone, flurochloridone, fluroxypyr, fomesafen, fosamrine, fosamtine, flamprop-isopropyl, flamprop-isopropyl-L, flufenpyr, flumiclorac-pentyl, flumipropyn, flumioxzim, flurtamone, flumioxzim, flupyrsulphuron-methyl, fluthiacet-methyl, glyphosate, glufosinate-ammonium, haloxyfop, hexazinone, imazamethabenz, isoproturon, isoxaben, isoxapyrifop, imazapyr, imazaquin, imazethapyr, ioxynil, isopropalin, imazosulphuron, imazomox, isoxaflutole, imazapic.

ketospiradox, lactofen, lenacil, linuron,

MCPA (2-(4-chloro-2-methylphenoxy)acetic acid), MCPA-hydrazide, MCPA-thioethyl, MCPB (4-(4-chloro-2-methylphenoxy)butanoic acid), mecoprop, mecoprop-P, mefenacet, mefluidide, mesosulphuron, metam, metamifop, metamitron, metazachlor, methabenzthiazuron, methazoie, methoroptryne, methyldymron, methyl isothiocyanate, metobromuron, metoxuron, metribuzin, metsulphuron, molinate, monalide, monalinuron, MSMA (monosodium methyl arsenate), metolachlor, metosulam, metobenzuron, naproanilide, napropamide, naptalam, neburon, nicosulphuron, norflurazon, sodium chlorate, oxadiazon, oxyfluorfen, oxysulphuron, orbencarb, oryzalin, oxadiargyl, propyzamide, prosulphocarb, pyrazolate, pyrazolsulphuron, pyrazoxyfen, pyribenzoxim, pyributicarb, pyridate, paraqual, pebulate, pendimethalin, pentachlorophenol, pentoxazone, pentanochlor, petroleum oils, phenmedipham, picloram, piperophos, pretilachlor, primisulphuron, prodiamine, profoxydim, prometryn, propachlor, propanil, propaquizafob, propazine, propham, propisochlor, pyriminobacmethyl, pelargonic acid, pyrithiobac, pyraflufen-ethyl, quinmerac, quinocloamine, quizalofop, quizalofop-P, quinchlorac, rimsulphuron, sethoxydim, sifuron, simazine, simetryn, sulphosulphuron, sulphometuron, sulphentrazone, sulcotrione, sulphosate, tar oils, TCA (trichloroacetic acid), TCA-sodium, tebutam, tebuthiuron, terbacil, terbumeton, terbuthylazine, terbutryn, thiazafluoron, thifensulphuron, thiobencarb, thiocarbazil, tralkoxydim, tri-allate, triasulphuron, tribenuron, triclopyr, tridiphane, trietazine, trifluralin, tycor, thidiazimin, thiazopyr, triflusulphuron, vernolate.

The invention furthermore relates to the use of the compositions according to the invention for protecting industrial materials against attack and/or destruction by microorganisms.

Industrial materials in the present context are understood to mean inanimate materials which have been prepared for use in industry. Industrial materials which are to be protected by the present invention against microbial change or destruction can be, for example, adhesives, sizes, paper and board, textiles, leather, wood, timber products, wood/plastic composites, paints, synthetic articles, cooling lubricants and other materials which can be attacked or destroyed by microorganisms. The range of materials to be protected also includes parts of production plants, for example cooling water circuits, which may be impaired by the proliferation of microorganisms. Industrial materials in the context of the present invention are preferably adhesives, sizes, papers and boards, leather, wood, timber products, wood-plastic composites, paints, cooling lubricants and heat transfer liquids; particularly preferred industrial materials are wood, timber products and wood-plastic composites (WPC).

Wood is to be understood as meaning, in particular: construction timber, wooden beams, railway sleepers, bridge components, jetties, vehicles made of wood, boxes, pallets, containers, telephone poles, wooden fences, wood lagging, windows and doors made of wood, joiners work and wood-based materials used in domestic construction or carpentry and joinery.

Timber products are to be understood as meaning, in particular: plywood, chipboard, fibre board, oriented strand board (OSB) or composite board.

Wood/plastic composite is to be understood as meaning, in particular: thermoplastically processable composites consisting of wood, plastic and additives.

Wood is particularly preferred.

Microorganisms capable of degrading or altering the industrial materials include, for example, bacteria, fungi, yeasts, algae and slime organisms. The compositions according to the invention preferably act against wood-destroying basidiomycetes, preferably holobasidiomycetes.

Here, mention may be made, in particular, of fungi of the following genera:

*Coniophora* such as *Coniophora puetana*,
*Lentinus* such as *Lentinus tigrinus*,
*Polyporus* such as *Polyporus versicolor*,
*Gloeophyllum*, such as *Gloeophyllum trabeum*,
*Poria*, such as *Poria placenta*,
*Coriolus*, such as *Coriolus versicolor*,
*Stereum*, such as *Stereum sanguinolentum*.

Particularly preferably, the compositions according to the invention act against species of the genera *Gloeophyllum, Coniophora, Coriolus, Stereum* or *Poria*. Very particularly preferably, the compositions according to the invention act against *Gloeophyllum trabeum, Coriolus versicolor, Stereum sanguinolentum* or *Poria placenta*.

In addition, the compositions to be used according to the invention act against wood-destroying and soft rot-causing ascomycetes and associated deuteromycetes, such as, for example:

species of the genus *Glenospora*, such as *Glenospora graphii*,
species of the genus *Chaetomium*, such as *Chaetomium globosum*,
species of the genus *Humicola*, such as *Humicola grisea*,
species of the genus *Petriella*, such as *Petriella setifera*,
species of the genus *Trichurus*, such as *Trichurus spiralis*,
species of the genus *Lecythophora*, such as *Lecythophora mutabilis*
species of the genus *Sclerophoma*, such as *Sclerophoma pityophila*
species of the genus *Aureobasidium*, such as *Aureobasidium pullulans*.

The invention furthermore relates to industrial materials, in particular wood, a timber product or a wood/plastic composite, comprising a) penflufen and its salts or acid addition compounds and
b) at least one compound selected from the group consisting of phenols, boron compounds, compounds of the formula (II)

$$((R^1R^2R^3R^4)N)_nX \qquad (II)$$

where
$R^1$ and $R^2$ may be identical or different and independently of one another represent $C_1$-$C_6$-alkyl and
$R^3$ and $R^4$ may be identical or different and independently of one another are selected from the group consisting of $C_6$-$C_{22}$-alkyl, $C_6$-$C_{22}$-alkenyl, $C_6$-$C_{24}$-aryl, $C_5$-$C_{20}$-cycloalkyl and radicals of the formula (IV)

$$-[CH_2-CH-O]_z-CH_2-CH_2-OH \qquad (IV)$$

where z=1, 2, 3, 4, 5, 6, 7, 8, 9 or 10 and
X represents an anion carrying a charge of n and
n is an integer greater than zero,
isothiazolinones, 3-iodo-2-propynyl alkylcarbamates, 3-iodo-2-propynyl cycloalkylcarbamates, 3-iodo-2-propynyl arylcarbamate and compounds of the formula (III)

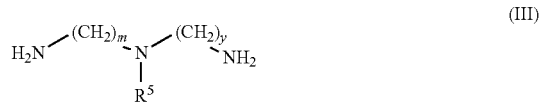

in which
$R^5$ represents $C_8$-$C_{18}$-alkyl, $C_8$-$C_{18}$-alkenyl or $C_5$-$C_{20}$-cycloalkyl and
m and y may be identical or different and represent a number 1, 2, 3, 4, 5 or 6, and their acid addition compounds.

The invention furthermore relates to a process for protecting industrial materials against attack and/or destruction by microorganisms, characterized in that at least one composition comprising a) penflufen and its salts or acid addition compounds and
b) at least one compound selected from the group consisting of phenols, boron compounds, compounds of the formula (II)

$$((R^1R^2R^3R^4)N)_nX \qquad (II)$$

where
$R^1$ and $R^2$ may be identical or different and independently of one another represent $C_1$-$C_6$-alkyl and
$R^3$ and $R^4$ may be identical or different and independently of one another are selected from the group consisting of $C_6$-$C_{22}$-alkyl, $C_6$-$C_{22}$-alkenyl, $C_5$-$C_{24}$-aryl, $C_5$-$C_{20}$-cycloalkyl and radicals of the formula (IV)

$$-[CH_2-CH_2-O]_z-CH_2-CH_2-OH \qquad (IV)$$

where z=, 2, 3, 4, 5, 6, 7, 8, 9 or 10 and
X represents an anion carrying a charge of n and
an s an integer greater than zero,
isothiazolinones, 3-iodo-2-propynyl alkylcarbamates, 3-iodo-2-propynyl cycloalkylcarbamates, 3-iodo-2-propynyl arylcarbamate and compounds of the formula (III)

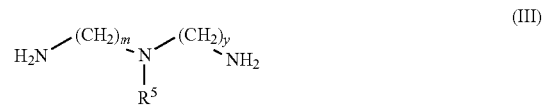

in which
$R^5$ represents $C_8$-$C_{18}$-alkyl, $C_8$-$C_{18}$-alkenyl or $C_5$-$C_{20}$-cycloalkyl
m and y may be identical or different and represent a number 1, 2, 3, 4, 5 or 6, and their acid addition compounds.

is allowed to act on the microorganism or its habitat, where the preferred embodiments mentioned above also apply here.

In the process according to the invention or in the use according to the invention, the compositions are applied to the industrial material preferably by painting, drenching, spraying, impregnating or in a different manner.

For wood, industrial impregnation processes, for example the vacuum, double vacuum, vacuum-pressure or pressure process, are preferred.

Wood-plastic composites can be prepared, for example, by mixing with input of thermal energy, in particular extruding or injection moulding, wood particles, a thermoplastic polymer and the compositions.

Wood composites can be treated, for example, by the glue incorporation method. Here, the composition according to the invention is, if appropriate, added in the form of a formulation of the glue liquor and this biocidally finished glue is applied in a customary manner to the chips, in particular applied using a nozzle (for example in the case of chip boards or OSB boards) or applied via rolls to the veneer (for example in the case of plywood). In the surface process, the composition according to the invention is, if appropriate, sprayed in the form of a formulation to the timber product or applied using a roll.

The use concentrations of the compositions according to the invention depend on the type and the occurrence of the microorganisms to be controlled, and on the composition of the material to be protected. The optimal rate of use can be determined by test series. In general, the use concentrations are in the range from 0.001 to 5% by weight, preferably from 0.005 to 1.0% by weight, of the composition and optionally other additives, based on the material to be protected.

In the industrial protection of wood, for example from 10 to 500 g of active compound are applied per $m^3$ of wood, preferably from 50 to 300 $g/m^3$, and optionally other additives.

Surprisingly, we have found novel compositions which act in a synergistic manner against microorganisms. This may improve the protection of industrial materials and reduce the amounts of active compounds which have to be employed.

The examples which follow serve to illustrate the invention by way of example and should not be interpreted as a restriction.

EXAMPLES

Synergism Tests

Mycelium pieces were punched out of a colony of the wood-destroying fungus in question and incubated on a malt extract/peptone-containing nutrient agar at 26° C. The growth of the hyphae with and without active compound was compared. The minimum inhibitory concentration (MIC) stated was the concentration at which the radial hyphae growth was suppressed completely.

The synergism was determined using the method described by Kull et al. (F. C. Kull, P. C. Eismann, H. D. Sylvestrowicz, R. L. Mayer, Applied Microbiology 1961, 9, 538-541). The following relationships apply:

$$\frac{Q_A}{Q_a} + \frac{Q_B}{Q_b} = SI$$

SI=1 means additivity
SI>1 means antagonism
SI<1 means synergism
$Q_a$=concentration of substance A which is the MIC
$Q_b$=concentration of substance B which is the MIC
$Q_A$=concentration of substance A in the concentration of A/B at which microbial growth is suppressed
$Q_B$=concentration of substance B in the concentration of A/B at which microbial growth is suppressed

Example 1

Combinations of Penflufen and 3-Iodo-2-propynyl N-butylcarbamate (IPBC) Against the Wood-Destroying Organism *Gloeophyllum Trabeum*

|  | MIC against *Gloeophyllum trabeum* (ppm) | SI |
|---|---|---|
| penflufen | 0.3 | — |
| penflufen:IPBC 9:1 | 0.3 | 0.90 |
| penflufen:IPBC 4:1 | 0.1 | 0.27 |
| penflufen:IPBC 7:3 | 0.3 | 0.71 |
| penflufen:IPBC 3:2 | 0.1 | 0.61 |
| penflufen:IPBC 1:1 | 0.3 | 0.52 |
| penflufen:IPBC 2:3 | 0.3 | 0.42 |
| penflufen:IPBC 3:7 | 0.3 | 0.32 |
| penflufen:IPBC 1:4 | 0.5 | 0.37 |
| penflufen:IPBC 1:9 | 0.7 | 0.30 |
| IPBC | 10.0 | — |

Example 2

Combinations of Penflufen and 4,5-dichloro-N-octylisothiazolin-3-one (DCOIT) Against the Wood-Destroying Organism *Poria placenta*

|  | MIC against *Poria placenta* (ppm) | SI |
|---|---|---|
| penflufen | 0.3 | — |
| penflufen:DCOIT 9:1 | 0.1 | 0.30 |
| penflufen:DCOIT 4:1 | 0.1 | 0.27 |
| penflufen:DCOIT 7:3 | 0.1 | 0.23 |
| penflufen:DCOIT 3:2 | 0.1 | 0.20 |
| penflufen:DCOIT 1:1 | 0.3 | 0.51 |
| penflufen:DCOIT 2:3 | 0.3 | 0.41 |
| penflufen:DCOIT 3:7 | 0.3 | 0.31 |
| penflufen:DCOIT 1:4 | 0.5 | 0.35 |
| penflufen:DCOIT 1:9 | 1.0 | 0.38 |
| DCOIT | 20.0 | — |

Example 3

Combinations of Penflufen and N-(3-aminopropyl)-N-dodecyl-1,3-propanediamine (Lonzabac) Against the Wood-Destroying Organism *Coriolus versicolor*

|  | MIC against *Coriolus versicolor* (ppm) | SI |
|---|---|---|
| penflufen | 0.5 | — |
| penflufen:Lonzabac 9:1 | 0.3 | 0.54 |
| penflufen:Lonzabac 4:1 | 0.3 | 0.48 |
| penflufen:Lonzabac 7:3 | 0.3 | 0.42 |
| penflufen:Lonzabac 3:2 | 0.5 | 0.60 |
| penflufen:Lonzabac 1:1 | 0.1 | 0.10 |
| penflufen:Lonzabac 2:3 | 0.1 | 0.08 |
| Lonzabac | 30.0 | — |

Example 4

Combinations of Penflufen and Didecyldimethylammonium Chloride (DDAC) Against the Wood-Destroying Organisms *Coriolus versicolor* and *Poria placenta*

|  |  | MIC (ppm) | | SI | |
|---|---|---|---|---|---|
|  |  | *Coriolus versicolor* | *Poria placenta* | *Coriolus versicolor* | *Poria placenta* |
| penflufen |  | 0.1 | 0.1 |  |  |
| penflufen:DDAC | 7:3 | 0.1 | 0.1 | 0.70 | 0.70 |
| penflufen:DDAC | 6:4 | 0.1 | 0.1 | 0.60 | 0.60 |
| penflufen:DDAC | 1:1 | 0.1 | 0.1 | 0.50 | 0.50 |
| penflufen:DDAC | 4:6 | 0.1 | 0.1 | 0.40 | 0.40 |
| penflufen:DDAC | 3:7 | 0.1 | 0.1 | 0.30 | 0.30 |
| penflufen:DDAC | 2:8 | 0.1 | 0.1 | 0.20 | 0.20 |
| penflufen:DDAC | 1:9 | 0.3 | 0.3 | 0.30 | 0.69 |
| DDAC |  | 60.0 | 100.0 |  |  |

Example 5

Combinations of penflufen and didecylmethylpoly(oxyethyl)ammonium Propionate (DDA Propionate) Against the Wood-Destroying Organisms *Stereum sanguinolentum* and *Poria placenta*

|  |  | MIC (ppm) | | SI | |
|---|---|---|---|---|---|
|  |  | *Stereum sanguinolentum* | *Poria placenta* | *Stereum sanguinolentum* | *Poria placenta* |
| penflufen |  | 3.0 | 0.3 |  |  |
| penflufen:DDA propionate | 8:2 | 0.7 | 0.1 | 0.19 | 0.27 |
| penflufen:DDA propionate | 7:3 | 0.7 | 0.3 | 0.17 | 0.70 |
| penflufen:DDA propionate | 6:4 | 3.0 | 0.1 | 0.64 | 0.20 |
| penflufen:DDA propionate | 1:1 | 3.0 | 0.1 | 0.55 | 0.17 |
| penflufen:DDA propionate | 4:6 | 3.0 | 0.3 | 0.46 | 0.40 |
| penflufen:DDA propionate | 3:7 | 1.0 | 0.5 | 0.12 | 0.50 |
| penflufen:DDA propionate | 2:8 | 3.0 | 0.7 | 0.28 | 0.47 |
| penflufen:DDA propionate | 1:9 | 3.0 | 0.7 | 0.19 | 0.24 |
| DDA propionate |  | 30.0 | 100.0 |  |  |

Example 6

Combinations of Penflufen and Benzalkonium Chloride Against the Wood-Destroying Organism *Poria Placenta*

|  | MIC against *Poria placenta* (ppm) | SI |
|---|---|---|
| penflufen | 0.3 | — |
| penflufen:benzalkonium chloride 1:1 | 0.3 | 0.50 |
| penflufen:benzalkonium chloride 4:6 | 0.3 | 0.40 |
| penflufen:benzalkonium chloride 3:7 | 0.5 | 0.50 |
| penflufen:benzalkonium chloride 2:8 | 0.5 | 0.34 |
| penflufen:benzalkonium chloride 1:9 | 1.0 | 0.34 |
| benzalkonium chloride | 100.0 | — |

Example 7

Combinations of Penflufen and a Mixture of Didecyldimethylammonium Carbonate and Didecyldimethyl Bicarbonate (Carboquat) Against the Wood-Destroying Organisms *Stereum sanguinolentum* and *Poria placenta*

|  |  | MIC (ppm) | | SI | |
|---|---|---|---|---|---|
|  |  | *Stereum sanguinolentum* | *Poria placenta* | *Stereum sanguinolentum* | *Poria placenta* |
| penflufen |  | 3.0 | 0.3 |  |  |
| penflufen:Carboquat | 7:3 | 3.0 | 0.3 | 0.7 | 0.7 |

-continued

|  |  | MIC (ppm) | | SI | |
|---|---|---|---|---|---|
|  |  | Stereum sanguinolentum | Poria placenta | Stereum sanguinolentum | Poria placenta |
| penflufen:Carboquat | 6:4 | 1.0 | 0.3 | 0.2 | 0.6 |
| penflufen:Carboquat | 1:1 | 3.0 | 0.3 | 0.6 | 0.5 |
| penflufen:Carboquat | 4:6 | 3.0 | 0.3 | 0.5 | 0.4 |
| penflufen:Carboquat | 3:7 | 3.0 | 0.5 | 0.4 | 0.5 |
| penflufen:Carboquat | 2:8 | 3.0 | 1.0 | 0.3 | 0.7 |
| Carboquat | 7:3 | 30.0 | 30.0 | | |

Example 8

Combinations of Penflufen and Boron Oxide ($B_2O_3$) Against the Wood-Destroying Organism *Coniophora putcana*

|  | MIC against *Coniophora puteana* (ppm) | SI |
|---|---|---|
| penflufen | 0.7 | — |
| penflufen:boron oxide 7:3 | 0.3 | 0.30 |
| penflufen:boron oxide 6:4 | 0.5 | 0.43 |
| penflufen:boron oxide 1:1 | 1.0 | 0.72 |
| penflufen:boron oxide 4:6 | 0.7 | 0.40 |
| boron oxide | 100 | — |

Example 9

Combinations of Penflufen and Boric Acid Against the Wood-Destroying Organisms *Coriolus versicolor* and *Gloeophyllum trabeum*

|  |  | MIC (ppm) | | SI | |
|---|---|---|---|---|---|
|  |  | Coriolus versicolor | Gloeophyllum trabeum | Coriolus versicolor | Gloeophyllum trabeum |
| penflufen | | 0.1 | 0.3 | | |
| penflufen:boric acid | 7:3 | 0.1 | 0.3 | 0.70 | 0.70 |
| penflufen:boric acid | 6:4 | 0.1 | 0.3 | 0.60 | 0.60 |
| penflufen:boric acid | 1:1 | 0.1 | 0.3 | 0.50 | 0.50 |
| penflufen:boric acid | 4:6 | 0.1 | 0.5 | 0.40 | 0.67 |
| penflufen:boric acid | 3:7 | 0.1 | 0.7 | 0.30 | 0.70 |
| penflufen:boric acid | 2:8 | 0.1 | 0.7 | 0.20 | 0.47 |
| penflufen:boric acid | 1:9 | 0.3 | | 0.30 | |
| boric acid | | 100.0 | 100.0 | | |

Example 10

Combinations of Penflufen and Sodium Borate Against the Wood-Destroying Organism *Poria placenta*

|  | MIC against *Poria placenta* (ppm) | SI |
|---|---|---|
| penflufen | 0.3 | — |
| penflufen:sodium borate 9:1 | 0.1 | 0.30 |
| penflufen:sodium borate 8:2 | 0.1 | 0.27 |
| penflufen:sodium borate 7:3 | 0.1 | 0.23 |
| penflufen:sodium borate 6:4 | 0.1 | 0.20 |
| penflufen:sodium borate 1:1 | 0.1 | 0.17 |
| penflufen:sodium borate 4:6 | 0.1 | 0.13 |
| penflufen:sodium borate 3:7 | 0.1 | 0.10 |
| penflufen:sodium borate 2:8 | 0.1 | 0.07 |
| penflufen:sodium borate 1:9 | 0.5 | 0.17 |
| sodium borate | 100.0 | — |

Example 11

Combinations of penflufen and o-phenylphenol Against the Wood-Destroying Organism *Gloeophyllum trabeum*

|  | MIC against *Gloeophyllum trabeum* (ppm) | SI |
|---|---|---|
| penflufen | 0.7 | — |
| penflufen:o-phenylphenol 7:3 | 0.7 | 0.70 |
| penflufen:o-phenylphenol 6:4 | 0.5 | 0.43 |
| penflufen:o-phenylphenol 1:1 | 1.0 | 0.72 |
| penflufen:o-phenylphenol 4:6 | 0.7 | 0.41 |
| penflufen:o-phenylphenol 3:7 | 0.7 | 0.31 |
| penflufen:o-phenylphenol 2:8 | 1.0 | 0.30 |
| penflufen:o-phenylphenol 1:9 | 3.0 | 0.47 |
| o-phenylphenol | 60.0 | — |

What is claimed is:

1. A synergistic mixture comprising a fungicidal composition for the inhibition of growth of basidiomycetes fungi, the composition comprising:

a) penflufen, salts of penflufen, acid addition compounds of penflufen, or any combination thereof; and b) at least one fungicidal compound selected from the group consisting of: o-phenylphenol and its alkali metal and alkaline earth metal salts sodium borate, boric acid, boron oxide, benzalkonium chloride, didecyldimethylammonium chloride, didecylmethylpoly(oxyethyl)ammonium propionate, didecyldimethylammonium carbonate, didecyldimethylammonium bicarbonate or a mixture of didecyldimethylammonium carbonate and didecyldimethylammonium bicarbonate, 4,5-dichloro-N-octylisothiazolin-3-one, 3-iodo-2-propynyl N-butylcarbamate, and N-(3-aminopropyl)-N-dodecyl-1,3-propanediamine, wherein components a) and b) are present in the composition at a weight ratio a):b) effective for providing fungicidal synergy against at least basidiomycetes fungi.

2. The composition according to claim 1, wherein the weight ratio effective for providing fungicidal synergy is a weight ratio of a) to b) of 1:50 to 50:1.

3. The composition according to claim 1, wherein the basidiomycetes fungi comprise *Gloeophyllum trabeum, Poria placenta, Coriolus versicolor, Stereum sanguinolentum*, and *Coniophora puteana*.

4. The composition according to claim 3, wherein the weight ratio effective for fungicidal synergy is a weight ratio of 1:20 to 20:1.

5. The fungicide according to claim 1, wherein the weight ratio of a) to b) is 10:1 to 1:10.

6. The composition according to claim 5, wherein the components a) and b) are present in at least the following weight ratios of a) to b):

9:1 to 1:9 with 3-iodo-2-propynyl N-butylcarbamate, 4,5-dichloro-N-octylisothiazolin-3-one, or sodium borate;

9:1 to 2:3 with N-(3-aminopropyl)-N-dodecyl-1,3-propanediamine;

7:3 to 1:9 with didecyldimethylammonium chloride, or o-phenylphenol;

8:2 to 1:9 with didecylmethylpoly(oxyethyl)ammonium propionate;

1:1 to 1:9 with benzalkonium chloride;

7:3 to 2:8 with the mixture of didecyldimethylammonium carbonate and didecyldimethylammonium bicarbonate;

7:3 to 4:6 with boron oxide; and

7:3 to 1:9 with boric acid.

7. A process for protecting industrial materials against attack and/or destruction by wood-destroying basidiomycetes wherein the wood-destroying basidiomycetes are species of the genera *Gloeophyllum, Coniophora, Coriolus, Sternum*, or *Poria*, the process comprising contacting the industrial materials with the composition according to claim 1.

8. The process according to claim 7, wherein the industrial materials are wood, timber products or wood-plastic composites.

9. An industrial material comprising wood and the composition according to claim 1.

* * * * *